(12) United States Patent
Langford (10) Patent No.: US 7,131,149 B2
(45) Date of Patent: Nov. 7, 2006

(54) FEMALE URINATION AID DEVICE (76) Inventor: Marlynn J. Langford, 485 Erving Jaboss Rd., Port Angeles, WA (US) 98362

( * ) Notice: Subject to any disclaimer, the term of this patent is extended or adjusted under 35 U.S.C. 154(b) by 90 days.

(21) Appl. No.: 11/097,030

(22) Filed: Mar. 31, 2005

(65) Prior Publication Data
US 2006/0218709 A1  Oct. 5, 2006

(51) Int. Cl.
A47K 11/00 (2006.01)

(52) U.S. Cl. ......................... 4/144.4; 4/144.2

(58) Field of Classification Search ...... 4/144.1–144.4; 604/329
See application file for complete search history.

(56) References Cited

U.S. PATENT DOCUMENTS

| 2,690,568 | A | * | 10/1954 | Willis ................. 4/144.4 |
| 3,572,318 | A | * | 3/1971 | Garland ................ 600/574 |
| 3,995,329 | A | | 12/1976 | Williams |
| 4,023,216 | A | | 5/1977 | Li |
| 4,608,046 | A | | 8/1986 | Towfigh |
| 4,626,249 | A | | 12/1986 | Hamey |
| 4,756,029 | A | | 7/1988 | Zieve |
| 4,857,064 | A | | 8/1989 | Mendoza |
| 4,936,838 | A | | 6/1990 | Cross et al. |
| 4,937,889 | A | | 7/1990 | Strickland |
| 4,937,890 | A | | 7/1990 | Tafur |
| 5,330,453 | A | | 7/1994 | Cornellier |
| 5,333,330 | A | | 8/1994 | Murtagh |
| 5,370,637 | A | | 12/1994 | Brodeur |
| 5,408,703 | A | | 4/1995 | Cicio |
| 5,742,948 | A | | 4/1998 | Cicio |
| 5,893,176 | A | | 4/1999 | Magiera et al. |
| 5,966,748 | A | | 10/1999 | Young |
| 6,434,757 | B1 | | 8/2002 | Filsouf |
| 6,460,200 | B1 | | 10/2002 | Mottale |
| 6,475,198 | B1 | | 11/2002 | Lipman |
| 6,537,262 | B1 | | 3/2003 | Thompson |
| 6,547,771 | B1 | | 4/2003 | Robertson |
| 6,669,675 | B1 | | 12/2003 | Lipman |
| 6,719,741 | B1 | | 4/2004 | Ching |

* cited by examiner

Primary Examiner—Charles E. Phillips
(74) Attorney, Agent, or Firm—Virginia P. Shogren, Esq.

(57) ABSTRACT

A water-resistant, collapsible female urination aid and absorbent wiping device comprising a funnel-shaped trough with first and second side walls, a center fan fold, and a discharge opening at the apex of pleats formed by the fan fold. Opposed flaps are secured to the external sides of the device to form opposed sleeves for insertion of a user's index and middle fingers. Upon separation of the fingers, the walls of the device spread open the fan fold portion to the desired width between the user's legs. Pleats direct and control the flow of urine towards the discharge opening; urine is directed out and away from the user. Internal surface of the device is water resistant; external surface is absorbent for wiping residual moisture from the vulva prior to disposal.

18 Claims, 6 Drawing Sheets

FEMALE URINATION AID DEVICE

FIELD

The invention relates to female urination aid devices, more particularly to disposable, funnel-type devices which allow women to direct the flow of urine in front of, and away from, their bodies while crouching or standing.

BACKGROUND

Due to the female anatomy, urine flow is controlled primarily through gravity and, unlike males, cannot be directed. This leads to difficulty controlling urine flow when women are faced with situations where toilet seats are either unavailable or undesirable for use. For example, when hiking or backpacking, a toilet seat is usually unavailable. A woman must lower her clothing, exposing much of her lower body to the outdoor elements, squat while holding the clothing, and simply hope that when the urine flows, it does not hit her clothing or shoes. Even after taking all precautions, there is no guarantee that clothing or shoes will not get wet with urine since the direction of the flow cannot be controlled. This is also the case with young girls who are unaccustomed to going to the bathroom without a toilet seat. Emergency stops along the road to go to the bathroom can be very difficult for women and girls (and their parents or caretakers) given the uncertainty in urine flow direction.

Women also are faced with situations when an available toilet seat is undesirable to sit on, such as in public restrooms, unisex restrooms, porta-potties, airplanes, tour buses, trains, and so on. These toilets are often dirty or otherwise in an unsanitary condition and women do not want to put their legs in contact with the toilet seat. To avoid sitting on an unsanitary toilet seat, women must pull down clothing and squat, holding themselves up over the toilet without touching any part of their legs to the toilet seat or rim. While maintaining this awkward and difficult squatting position, women must release their bladder muscles and hope that the urine stream will reach the toilet bowl without hitting the toilet seat, toilet rim, their legs, clothes and/or the bathroom floor. It is difficult for women to partially squat and release urine at the same time. The leg muscles are unaccustomed to holding a woman's body in place while squatting in a backwards direction with the width of the leg separation limited by pulled down clothing such as pants and underwear. It is a balancing act and can be very stressful if urine flows onto the woman's body or clothes.

In addition, while toilet seats are common in the United States, many cultures in other countries do not customarily build bathrooms designed for women and/or do not have toilet seats installed in bathrooms. Most women have encountered bathrooms while traveling outside of the United States that are designed for the male anatomy in the sense that the urine is to be directed towards a target—whether the target is a urinal or a hole in the floor over which a woman must straddle. Without the natural ability to direct urine flow, these types of bathrooms present similar problems for women—they are forced to remove or pull down clothing, straddle a target that is usually placed in front of them, and release their bladder muscles without knowing where the flow of urine will be directed other than in a generally downward direction, controlled by gravity alone.

There also are instances when a woman may not be physically comfortable, or physically able, to sit on a toilet seat, such as following surgery. Examples include hip injury, post hip surgery, arthritis, or any condition causing pain or discomfort to a woman if she has to bend into a squatting or sitting position. It is also awkward and difficult for women to provide urine samples in a medical setting since the woman must hold a cup underneath her vulva and over the toilet bowl hoping that the urine stream will find its way into the cup and not elsewhere.

Situations where toilet seats are not available or in an undesirable/unsanitary condition are often accompanied by a confounding problem of a lack of toilet paper with which to wipe the vulva when finished urinating. Given the female anatomy, women are unable to tap the last drops of urine from their vulva and must instead use something to wipe the residual moisture away. If toilet paper is unavailable, a woman must let the urine be absorbed into the underwear leaving an uncomfortable sensation of moisture.

There are female, urination aids and devices in the prior art. For example, U.S. Pat. Nos. 5,408,703 and 5,742,948, both to Cicio, disclose a disposable funnel made of water absorbent paper. The Cicio funnel can be folded flat for storage by means of two opposed creases that define the tapered vertical front and back profiles of the funnel. To use it, pressure is applied to the creases to flex open the funnel. Use of the Cicio funnel is tricky. The funnel must be held by a user around its exterior and pressure must be carefully maintained across the creases to flex and keep the device open during use. The urine flow must be carefully directed into the funnel opening, since the Cicio funnel absorbs urine it can collapse. Further, the changes in weight due to variable urine flow requires a very deft amount of flex pressure on the creases to keep the funnel uniformly open. Further, if it leaks and/or overflows, the user's hand will get wet with urine. The device is also designed to absorb the urine flow, leaving a wet funnel when finished.

Accordingly, there is an unmet need for a disposable female urination device to direct urine which is both sufficiently waterproof and absorbent to serve the dual purposes of directing the urine flow while protecting the user's hand from contact with urine, on the one hand, and thereafter being used to wipe the vulva in lieu of toilet paper, on the other hand, and is simple and comfortable to use by an adult woman, girl, or the caretaker of a girl in a variety of conditions and situations where toilet seats are unavailable or unsuitable.

THE INVENTION

Summary, Including Objects and Advantages

The inventive female urination device comprises a generally funnel-shaped trough made of disposable, pliable, paper-based material with a first side wall, a second side wall, a center fan fold portion, and a discharge opening at the apex of pleats formed by the fan fold. In the preferred embodiment, the fan fold comprises two adjoining, tapered, identical pleats formed by spaced, alternating valley and mountain creases. The device folds flat for carry and storage.

The device further includes opposed flaps extending from top margins of the first and second side walls. The flaps are folded and secured to the external sides of the first and second side walls to form opposed finger sleeves. A user of the device inserts her index and middle fingers into the opposed slot openings formed by finger sleeves after inverting her hand so that the palm of her hand is facing upwards. The device may be placed on the left or right hand depending on the user's preference. Once fingers are inserted into the device, the user separates her index and middle fingers thereby separating the first and second walls of the device and spreading open the fan fold portion.

The user may then hold the device in position between her legs and adjacent and/or touching her vulva while spreading her legs and/or crouching at the desired or most comfortable angle. The fan fold is spread to the desired width depending on the shape of the user's body so as to comfortably fit within the space between the user's thighs immediately below the vulva. The pleats of the fan fold direct and control the flow of urine towards the discharge opening at the apex of the fan fold. The urine is projected out of the discharge opening and away from the user's body.

The interior walls of the device are water resistant, e.g., thinly coated with wax, a thin plastic film, a plasticized or resin-treated paper, or the like, so as to not be immediately permeable to urine passing through the device. The outside walls of the device are absorbent to water/urine so that the user of the device may remove the device from her fingers when finished urinating, and use the exterior of the device to wipe residual moisture from the vulva prior to disposal.

The device is used by one hand, freeing the other hand to help support the user of the device, if desired. The user may stand almost in an upright position when using the device to maximize balance and control. The device may optionally be held in position by another person, such as a parent or caretaker, when assisting a girl. Different sizes of the device may be made for girls, as opposed to women.

The device is collapsible to a flat form, lightweight, easy to carry, such as in a pant pocket or purse, and is easy to store. It may be packaged separately or dispensed by means of a container with a slot opening such as in the manner of tissues.

BRIEF DESCRIPTION OF THE DRAWINGS

The invention is described in more detail with reference to the drawings, in which.

DETAILED DESCRIPTION, INCLUDING THE BEST MODES OF CARRYING OUT THE INVENTION

The following detailed description illustrates the invention by way of example, not by way of limitation of the scope, equivalents or principles of the invention. This description will clearly enable one skilled in the art to make and use the invention, and describes several embodiments, adaptations, variations, alternatives and uses of the invention, including what is presently believed to be the best modes of carrying out the invention.

In this regard, the invention is illustrated in the several figures, and is of sufficient complexity that the many parts, interrelationships, and sub-combinations thereof simply cannot be fully illustrated in a single patent-type drawing. For clarity and conciseness, several of the drawings show in schematic, or omit, parts that are not essential in that drawing to a description of a particular feature, aspect or principle of the invention being disclosed. Thus, the best mode embodiment of one feature may be shown in one drawing, and the best mode of another feature will be called out in another drawing.

All publications, patents and applications cited in this specification are herein incorporated by reference as if each individual publication, patent or application had been expressly stated to be incorporated by reference.

Figure 1:
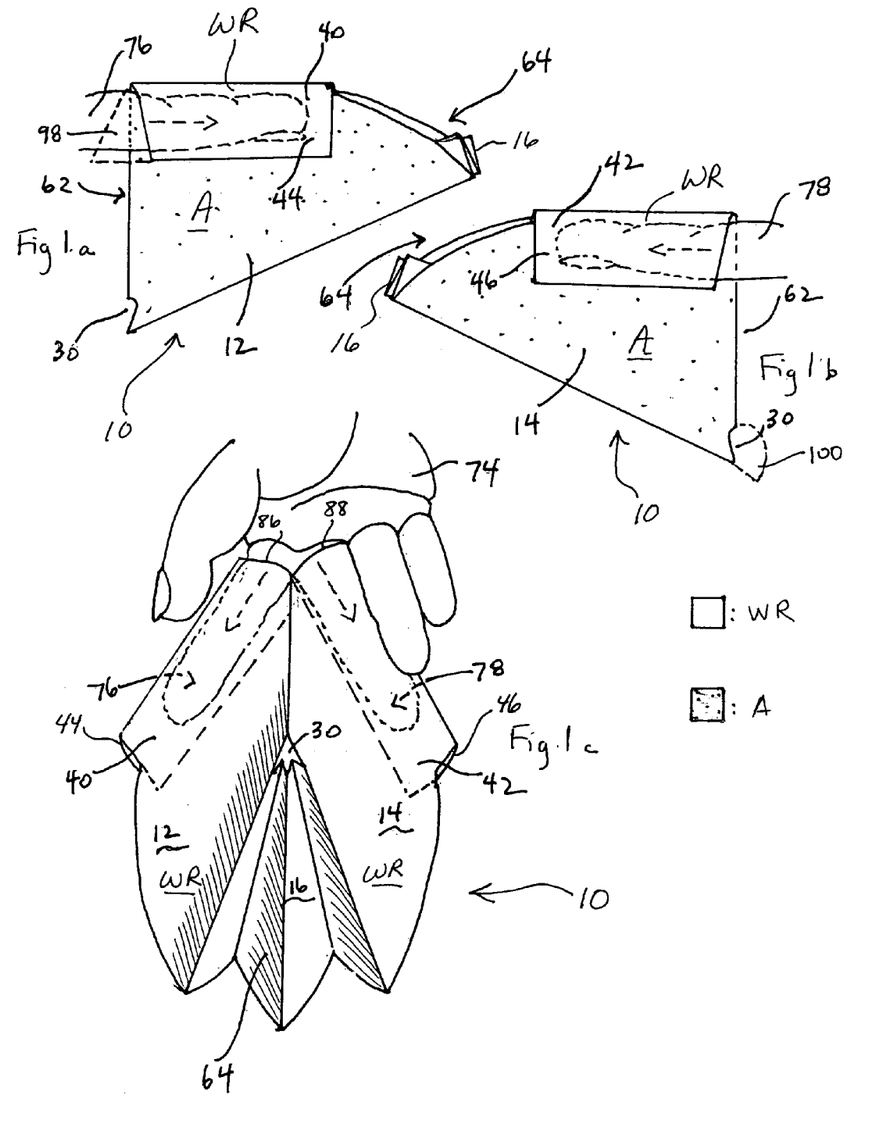
FIG. 1a is a side elevation view of the right side of the device in an open configuration.
FIG. 1b is a side elevation view of the left side of the device in an open configuration.
FIG. 1c is a top view of the device in an open configuration on a user's right hand fingers.

Referring to FIGS. 1a and 1b, an example of the preferred embodiment of the present invention is illustrated and generally indicated by the reference numeral 10. The device 10 is generally triangular shaped with a first side wall 12, a second side wall 14, and a central fan fold 16. First side wall 12 and second side wall 14 are joined at a back crease or seam 18. First side wall 12 joins fan fold 16 forming valley crease 20, and second side wall 14 joins fan fold 16 forming valley crease 22.

In a first embodiment, the fan-fold section 16 has a first mountain crease 24 and a second mountain crease 26 with center valley crease 28 between mountain creases 24 and 26. First side wall 12 and mountain crease 24 meet to form valley crease 20, and second side wall 14 and second mountain crease 26 meet to form valley crease 22. One skilled in the art will appreciate that the number of panels and creases in the fan fold section 16 can be increased or decreased to accommodate changes in size and taper of the device 10.

FIG. 1a shows a right side elevation view of the device 10 with first side wall 12 and finger sleeve 40. Index finger 76 is inserted through slit opening 86 at the margin of flap 44 that is folded over to form finger sleeve 40. The discharge opening 30 is at the base of the discharge end 62 of the device 10. The exterior of side wall 12 is made of absorbent material marked "A". The exterior of the sleeve-forming flap 44 encircling the index finger 76 is coated with or made of urine and water-resistant material marked "WR." Fan fold 16 pleats are visible at the front end 64 of the device 10.

FIG. 1b shows a left side elevation view of the device 10 with second side wall 14 and finger sleeve 42. Middle finger 78 is inserted through slit 88 at the margin of flap 46. The discharge opening 30 is at the base of discharge end 62. The exterior of side wall 14 is also made of absorbent material marked "A". The exterior of the sleeve-forming flap 46 encircling middle finger 78 is coated with or made of urine- and water-resistant material marked "WR."

FIG. 1c shows a top view of the device 10 with fingers 76, 78 inserted inside finger sleeves 40 and 42. The interior portions of finger sleeves 40, 42, side walls 12, 14, and fan fold section 16 are made of water-resistant material marked WR. The middle and fourth fingers also could be inserted into finger sleeves 40, 42.

The discharge opening 30 is at the apex of the fan fold section 16, formed by the convergence of seam 18, side walls 12, 14, valley creases 20, 22 and 28, and mountain creases 24 and 26. First side wall 12 and second side wall 14 have finger sleeves 40 and 42 respectively at their upper margins that a user accesses by slots 86, 88.

Prior to use, a user would insert the index and middle fingers in parallel with the device 10 in the closed configuration; then spread the fingers open to a position as shown in FIG. 1c.

Figure 2:
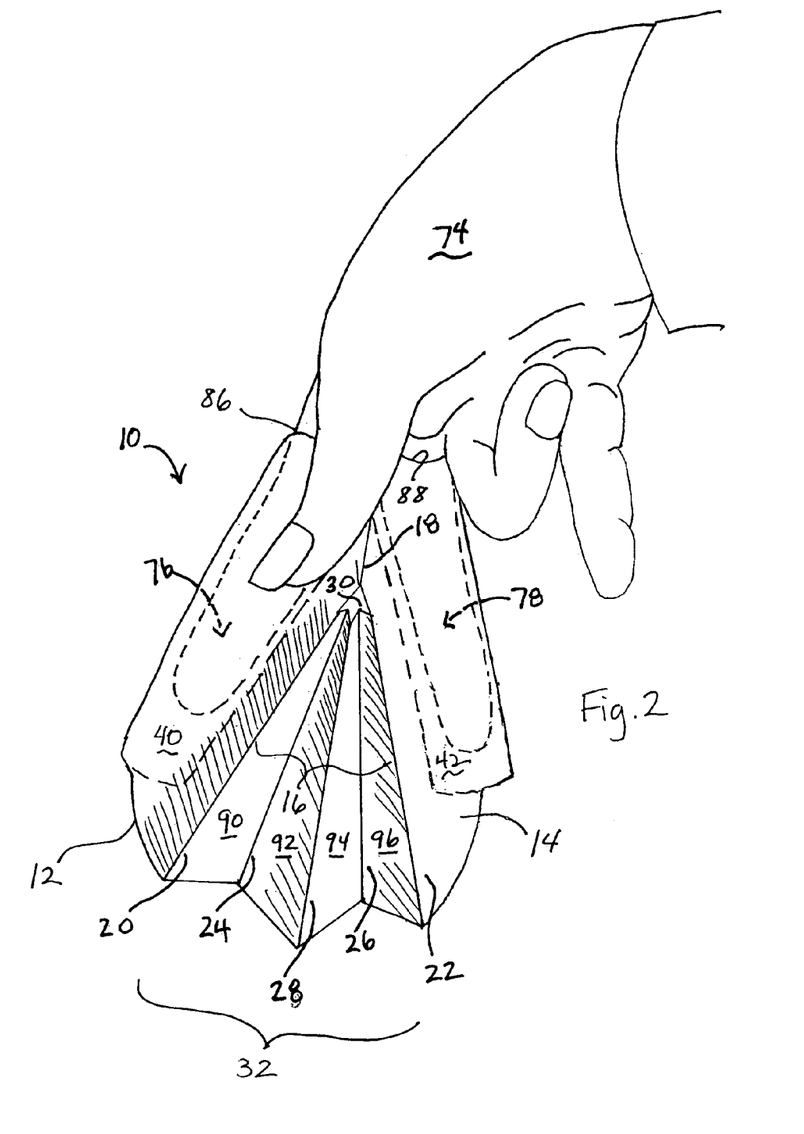
FIG. 2 is an isometric view of the device in an open or usable configuration held by a user's right hand.
Figure 3:
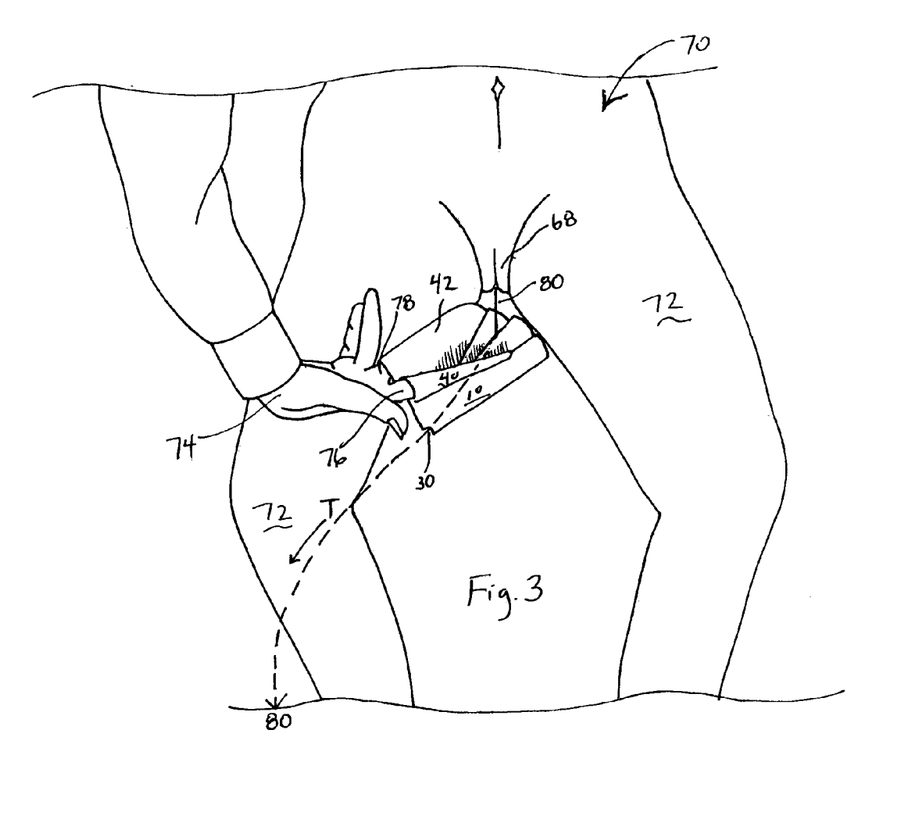
FIG. 3 is a plan view of the device in use.

FIGS. 2 and 3 show the device 10 in use. As shown in FIG. 2, the device 10 is held in position by the insertion of a user's index finger 76 and middle finger 78 into the opposed finger sleeves 40, 42. The flexibility of the fan fold section 16 permits the device 10 to be opened to the desired width by spreading the index finger 76 and middle finger 78 when the device is held in position between a user's 70 legs 72. Fan fold 16 comprises multiple tapered, joined panels 90, 92, 94, 96 forming a pleated urine catchment and run-off section.

As shown in FIG. 3, the device 10 is held in position between the user's 70 legs 72 adjacent to the vulva 68. Referring to FIG. 2, mountain creases 24 and 26 function to deflect and direct urine to flow into and down valley creases 20, 22 and 28. Valley creases 20, 22, and 28 are positioned at a slightly downward angle when the device 10 is held in position between the legs 72 such that urine 80 flows by gravitational pull in a downward direction. Valley creases 20, 22 and 28 direct urine to discharge opening 30 out of which urine 80 flows in trajectory "T" well away from the user 70 as shown in FIG. 3.

Referring again to FIGS. 2 and 3, to use the device 10, a user 70: 1) partially inverts her hand 74 so that her palm is facing generally upwards; 2) while holding the device 10 in the opposite hand, the user 70 inserts her index finger 76 and middle finger 78 from her free hand into finger sleeves 40 and 42 via finger slots 86, 88; 3) spreads her index and middle fingers 76, 78 apart to open device 10; 4) positions the device 10 between her legs 72 (having previously removed or pulled down clothing not shown in FIG. 3); 5) widens or narrows the device 10 to a desired width so that portions of the upper periphery 32 of the device 10 touch the legs 72 and are comfortably surrounding the vulva 68; 6) releases her bladder muscles to commence urination, adjusting the direction of the device 10 as desired to direct urine flow 80; 7) continues to hold the device 10 in position until urination is complete; and, 8) upon completion, removes the device from her fingers and optionally uses the exterior absorbent portions of the device 10 (shown in FIGS. 1a and 1b) to wipe residual moisture from the vulva 68 prior to disposal of the device 10.

As shown in FIG. 3, during use, the user's hand 74 is positioned behind the device 10 with palm of the hand 74 faced generally upwards and fingers 76, 78 inserted inside finger sleeves 40, 42 pointed in the direction of the user's 70 legs 72.

As shown in FIG. 3, one advantage of the device 10 is the relatively upright standing position of the user 70 while urinating. A user does not have to bend backwards and squat as is the case when a user is attempting to hold herself up while urinating into a toilet bowl. Instead, she may center her gravity over her legs 72.

Figures 4A, 4B, 4C:
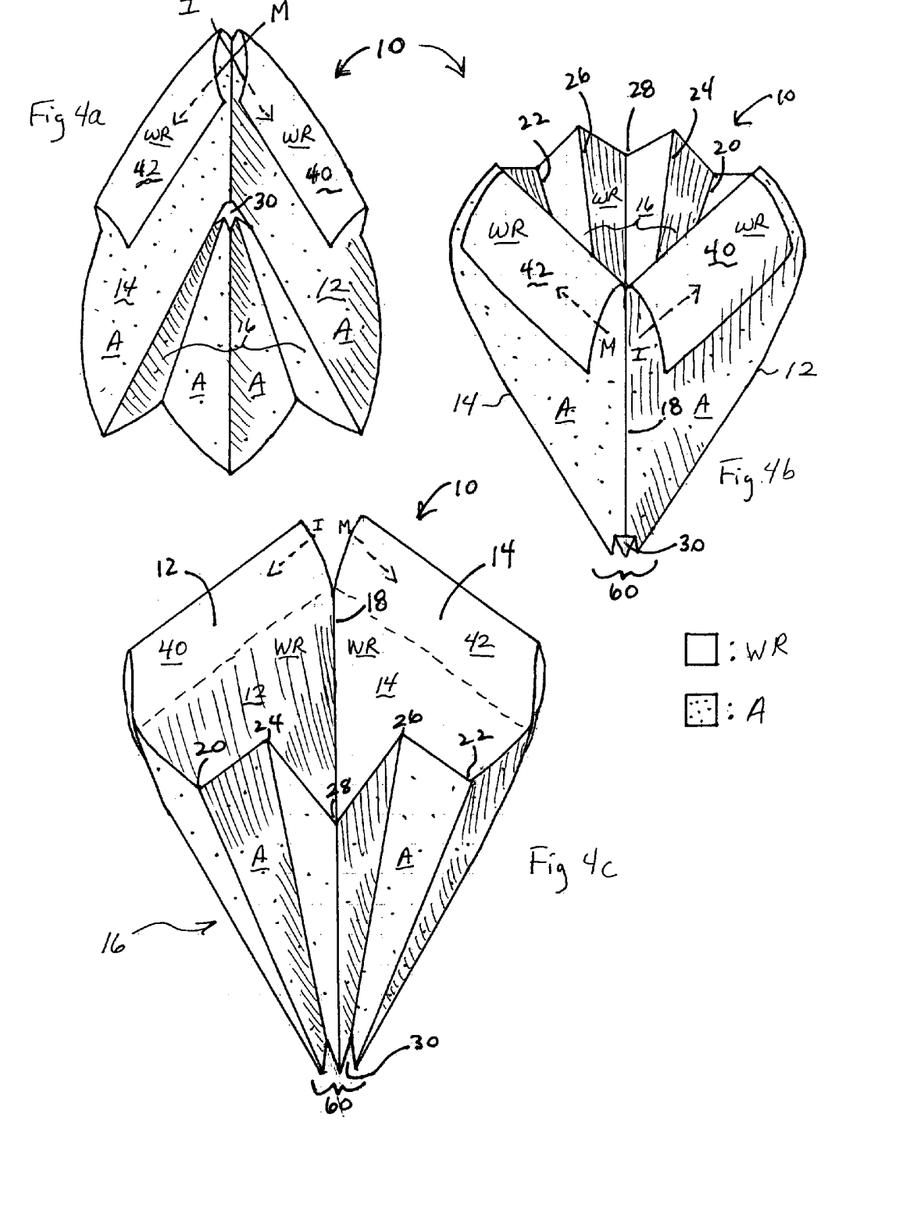
FIG. 4a is a bottom view of the device in an open configuration
FIG. 4b is a front elevation view of the device in an open configuration.
FIG. 4c is a rear elevation view of the device in an open figuration.

FIGS. 4a through 4c show various views of the device 10 in the open configuration. FIG. 4a shows a bottom view of the device 10 from the front in the open configuration. While in use, a user's index finger (not shown) would be inserted in direction "I" into finger sleeve 40, and the middle finger (not shown) would be inserted in direction "M" into finger sleeve 42. If the user is left-handed, the finger positions are reversed; i.e., an index finger would be inserted in the "M" direction into finger sleeve 42, and the middle finger would be inserted in direction "I" into sleeve 40.

The exterior portions of side walls 12, 14 and fan fold 16 are absorbent and marked "A." The exterior portions of finger sleeves 40 and 42 are water resistant and marked "WR."

FIG. 4b shows a front elevation view of the device 10 in the open configuration. Back seam 18 joins side walls 12, 14. In use, a right-handed user's index finger (not shown) would be inserted in direction "I" into finger sleeve 40, and the middle finger (not shown) would be inserted in direction "M" into finger sleeve 42. The exterior portions of side walls 12 and 14 are absorbent and marked "A." The exterior portions of finger sleeves 40 and 42 and the interior portion of fan fold section 16 are water resistant and marked "WR."

FIG. 4c shows a rear elevation view of the device 10 in the open configuration. Back seam 18 joins side walls 12, 14. In use, a right-handed user's index finger (not shown) would be inserted in direction "I" into finger sleeve 40, and the middle finger (not shown) would be inserted in direction "M" into finger sleeve 42. The exterior portions of fan fold 16 are absorbent and marked "A." The interior portions of finger sleeves 40 and 42 and side walls 12, 14, are water resistant and marked "WR."

Figure 5:
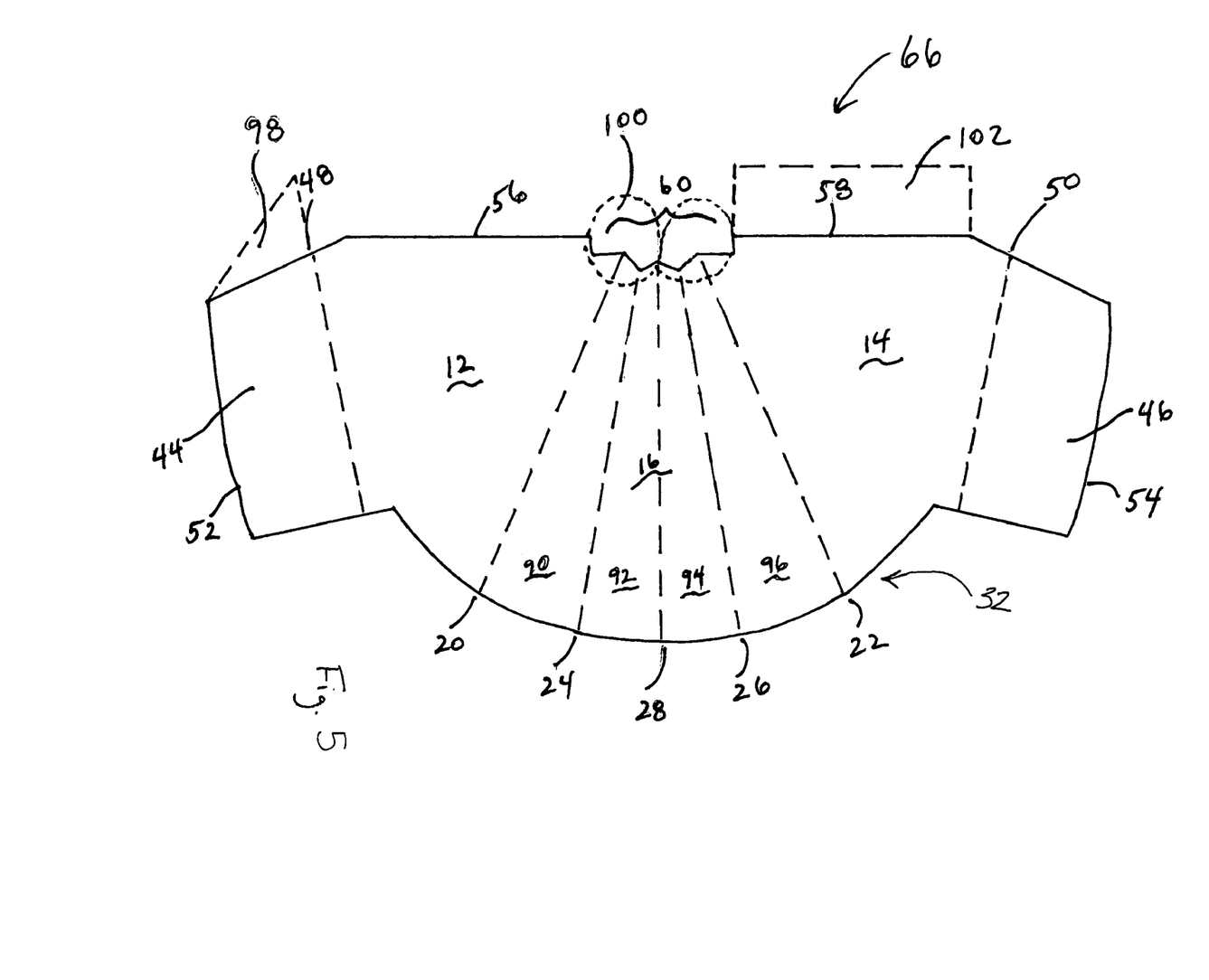
FIG. 5 is a top plan view of a pattern for the device.

FIG. 5 shows a pattern 66 for the device 10 drawn to about one-half scale. The pattern 66 is symmetrical with opposed flaps 44 and 46 and fold lines 48 and 50 to form finger sleeves 40 and 42 (shown in FIG. 1c and FIG. 2). The finger sleeves 40 and 42 are formed by folding flaps 44 and 46 at fold lines 48 and 50, respectively, and attaching edges 52 and 54 to the exterior portion of side walls 12 and 14, respectively. The sleeves 40, 42 pop open at fold lines 48 and 50 when a user inserts her fingers.

Seam 18, shown in FIG. 4c, is formed by joining edge 56 of side wall 12 to edge 58 of side wall 14, forming a collapsible seam. Alternately, seam 18 could be formed by one or more tabs 102 extending down portions or all of the margins of edges 56 and/or 58, said tabs overlapping portions of at least one of the opposed side walls 12, 14, and permitting joining of the side wall 12, 14 to form the seam 18. Tabs along portions of the margins of the fan fold section 16 also could be used to join the fan fold section 16 to side walls 12, 14.

The pattern 66 includes folding lines to form valley creases 20, 22 and 28 and mountain creases 24, 26 of fan fold 16. Apex 60 is configured in a jagged, W-shape to permit formation of fan fold 16 creases 20, 24, 28, 26 and 22. It should be understood that apex 60 could be of any suitable shape and construction to direct urine in a stream away from the user 70. For example, the apex 60 and/or terminus of side walls 12, 14 could include one or more alternate, opposed stream control flaps 100 as shown in FIG. 1b to form a slit-shaped opening. Periphery 32 in one embodiment is curved in shape.

Attachment of flaps 44, 46 to side walls 12 and 14, respectively, can be made by any suitable method, for example such as by any suitable adhesive, tape, or thermal bonding, and preferably in a manner that will facilitate biodegradation of the device 10 after use. Attachment of side walls 12 and 14 at edges 56 and 58 to form the back seam 18 also can be achieved by any suitable method including adhesive, tape, or thermal bonding.

Pattern 66 is preferably made of disposable, celluloisic, non-woven, paper-based materials that also are readily biodegradable. As shown in FIGS. 1a, 1b, 4a and 4b, the outer surface of the device 10 comprises soft, absorbent paper-based material for use to wipe after urination. The interior surface of pattern 66 comprises one or more water-resistant or water-repellant layers to prevent the device from softening or falling apart during use and preventing urine from seeping onto the user's fingers or hand. In the first, preferred embodiment, pattern 66 for the device 10 can be made from butcher paper that is absorbent on its exterior surface, and thinly coated with wax on the interior surface. In a second embodiment, thin, disposable material formed of a thin plastic sheet bonded to an absorbent, non-woven material can be used. Alternately, the device 10 could be made of a rigid plastic permitting cleansing of the device 10 between uses and thereby permitting reuse.

It should be noted that various modifications to the pattern 66 and device 10 construction are possible within the scope of this invention. For example, flaps 44, 46 could be of different lengths, shapes, or have an extension as shown in FIG. 1a with alternate sleeve extension 98 for ease of finger insertion. Fingers could extend through the ends of finger sleeves 40, 42, or the sleeves could be sealed at their terminus. Flaps 44, 46 could be of any suitable width and could be designed for insertion of fingers other than the index and middle fingers. For example, one sleeve could be formed for thumb insertion; the opposed sleeve could be formed for insertion and retention of the device 10 by one or more of the other fingers, e.g., middle and fourth fingers or fingers of the opposite hand.

Finger sleeves 40, 42, also could be formed using separate pieces of material, as opposed to folding down flaps 44, 46. In that event, finger sleeves 40, 42 may be formed and positioned at any suitable point on side walls 12, 14, such as at a 90-degree angle to the fan fold section 16. The margins 86, 88 of finger sleeves 40, 42, could also be rounded, or off-set, or of any other suitable design to allow for ease of finger insertion and removal.

Other structures could be used to hold the device in the open configuration; a non-limiting example is opposed extension tabs extending from the upper margins of the side walls 12, 14 that a user may hold with both hands to stretch open the fan fold section 16 during use. Alternately, a user may hold the device with both hands at opposed upper margins of the side walls 12, 14 in a device 10 with or without finger sleeves 40, 42 to stretch open the fan fold section 16 during use.

Periphery 32 is curved in shape for optimum comfort and fitting when held in position between a user's 70 legs 72. However, the periphery 32 may be of any suitable shape and/or may have a design on its edge, such as scallops, and may comprise softer material for comfort when in contact with the user's body.

Other variations are possible; for example, portions of the fan fold 16 may have higher water-resistant qualities. The apex 60 portion of the fan fold 16 may have a thicker coat of wax or water resistant material applied to permit more contact with urine without becoming moist, to keep the device from losing its structural strength and form at the discharge opening 30 (shown in FIG. 1c), and/or to ensure a desired trajectory of urine 80 passing through the discharge opening 30 as shown in FIG. 3.

The pattern 66 also could be limited to a single crease extending from the apex 60 to the periphery 32. The fan fold 16 could alternately have more than two mountain creases; or the fan fold 16 could comprise reversed valley and mountain creases (e.g., a single, center mountain crease with valley creases on either side). In the preferred embodiment, the height of the mountain creases is approximately 1 inch above the valley when the device 10 is in the closed, flattened, position; however, the height, number, and width of the pleats could be of any suitable number and dimension.

The pleats 20, 24, 28, 26 and 22 of the fan fold 16 may be formed through manual folding of the device pattern 66, and/or through heat applied to the device 10 in the collapsed position so as to form and set the pleats.

The device 10 may optionally include printed indicia to assist a user; for example, flaps 44, 46 could have one or more arrows printed on them showing direction of finger insertion; and fan fold 16 could have one or more arrows printed on creases 20, 22, and 28 showing direction of urine flow through the device 10.

The device 10 is preferably stored and/or packaged in a flat, collapsed, closed position with pleats pressed together as a travel package. The device 10 may be packaged in any suitable manner, including singly, in small numbers, or enclosed in a container with one or more openings, such as slot openings, for ease of dispensing.

Figure 6:
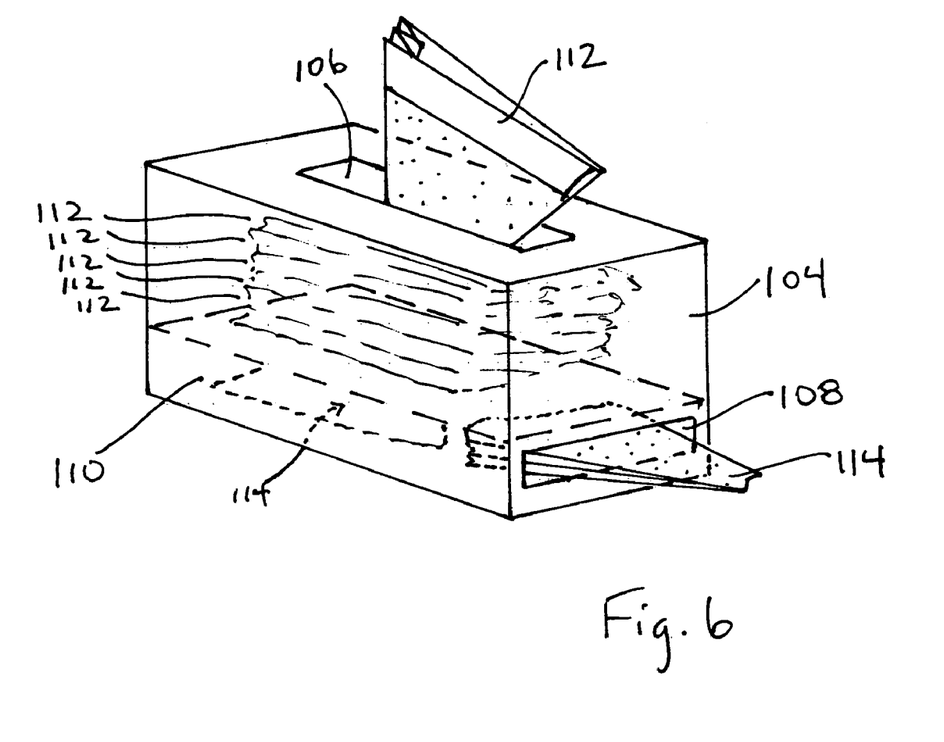
FIG. 6 is an isometric view of a dispenser and disposal container for the device.

Referring to FIG. 6, the device may also be packaged in a container 104 that includes a first slot opening 106 for dispensing of a fresh device 112, and a second slot opening 108 into a disposal space 110 for disposal of a used device 114. As shown in FIG. 6, the dispensing container may have a slot opening 106 on its top end for dispensing the device 10 one at a time, and a second slot opening 108 to an enclosed disposal space 110 at the base of the container 104 for insertion of the device 114 after use in the event the device 10 cannot otherwise be discarded (such as when traveling by car). When all devices 10 have been used, the entire container 104, including used devices 10 retained in the disposal space 110, may be discarded when convenient.

INDUSTRIAL APPLICABILITY

It is clear that the inventive female urination aid device of this application has wide applicability to the feminine hygiene industry, namely to controlling and directing urine flow when women are faced with situations where toilet seats are either unavailable or undesirable for use, and/or when a woman is not physically comfortable or physically able to sit on a toilet seat. The device is water-resistant on its interior surface, but absorbent on the exterior surface, allowing for use of the device to wipe residual moisture after use and before disposal in situations where toilet paper is not available.

The device may be used in a variety of situations, from traveling in locations that do not have adequate bathroom facilities for women, to outdoor use while hiking or backpacking, to emergency bathroom stops along the road when driving. The collapsible device is simple in design, easy to store, carry and use, and keeps the user's hands and body clean from urine. Thus, the inventive device has the clear potential of becoming adopted as the new standard device for assisting women in urinating when it is not possible, because of proximity, toilet seat conditions, physical pain and/or injury, to sit on a toilet seat.

It should be understood that various modifications within the scope of this invention can be made by one of ordinary skill in the art without departing from the spirit thereof and without undue experimentation. For example, the fan fold portion can have a wide range of designs to provide the functionalities disclosed herein. The pleats can be reversed; the angle of convergence can be modified. There are also a variety of different paper-based materials that could be used and a variety of means for providing water resistance to the interior portion of the device, and water absorbency to the exterior. This invention is therefore to be defined by the scope of the appended claims as broadly as the prior art will permit, and in view of the specification if need be, including a full range of current and future equivalents thereof.

PARTS LIST

10 Female Urination Aid Device
12 First side wall
14 Second side wall
16 Fan fold
18 Seam
20 valley crease joining 12 to 16
22 valley crease joining 14 to 16
24 first mountain crease
26 second mountain crease
28 center valley crease/trough
30 Discharge opening
32 Periphery
40 Finger sleeve
42 Finger sleeve
44 flap
46 flap
48 Fold line
50 Fold line
52 Attaching edge
54 Attaching edge
56 edge of side wall 12
58 edge of side wall 14
60 apex
62 discharge end
64 front end
66 pattern
68 vulva
70 user
72 legs
74 hand
76 index finger
78 middle finger
80 urine flow
86 finger slot
88 finger slot
90 panel
92 panel
94 panel
96 panel
98 alternate sleeve extension
100 alternate stream control flaps
102 alternate joining tab
104 container
106 first slot opening
108 second slot opening
110 disposal space
112 fresh device
114 used device
A—absorbent; WR—water resistant; T—urine trajectory; I—index finger insertion; M—middle finger insertion

The invention claimed is:

1. A water-resistant, collapsible, female urination aid and absorbent wiping device comprising:
   a) generally triangular-shaped first and second spaced side walls, said side walls having a generally inclined bottom edge, a generally vertical forward edge, and an upper margin;
   b) said side walls are joined along their bottom edges by a generally triangular-shaped center fan fold section;
   c) said side walls and fan fold section are made of flexible, self-supporting material having an external surface and an internal surface;
   d) said first and second side walls are joined along the forward edge to form a collapsible seam;
   e) said fan fold section comprising at least one pair of joined, converging panels forming at least one collapsible and expandable pleat for spacing said side walls apart to receive urine onto said fan fold's internal surface, said fan fold section converging toward a second apex end adjacent the seam;
   f) a discharge opening formed adjacent the intersection of said forward edge and said fan fold section apex for discharging urine from said device away from a user;
   g) at least one collapsible finger sleeve positioned on the exterior surface of each of said side walls, each of said finger sleeves formed to permit insertion and retention of at least one finger of a user's hand, said finger sleeves permitting opening of said upper margin of said device to receive urine;
   h) at least a portion of said internal surface having water-resistant properties; and,
   i) at least a portion of said exterior surface having water-absorbent properties to provide a post-urination wiping surface.

2. The device of claim 1 wherein said material is disposable.

3. The device of claim 1 wherein said water-resistence is provided by a material selected from a wax, a resin, and/or thin plastic sheet material.

4. The device of claim 1 wherein at least a portion of said external surface comprises water absorbent fibrous material.

5. The device of claim 4 wherein said fibrous material is a cellulosic non-woven material.

6. The device of claim 1 wherein different sections of said internal surface have different water-resistant properties.

7. The device of claim 1 wherein different sections of said external surface have different water-absorbent properties.

8. The device of claim 1 wherein said material includes informational indicia disposed on the external and/or internal surfaces.

9. The device of claim 1 wherein one or more of said side walls include at least one tab extending from at least one of the margin of the forward edge and/or the bottom edge to permit joining of the first and second side walls to form the collapsible seam and/or to permit joining of the fan fold section to at least one side wall.

10. The device of claim 1 wherein the fan fold section comprises a plurality of joined pleats formed by one or more alternating valley and mountain creases.

11. The device of claim 1 wherein said one or more finger sleeves comprise a first finger sleeve positioned adjacent the upper margin of the first side wall, and an opposed second finger sleeve positioned adjacent the upper margin of the second side wall.

12. The device of claim 11 wherein said finger sleeves are formed by opposed tabs extending from the upper margin of the first and second side walls; said tabs folded over and adhered to the external surface of the first and second side walls.

13. The device of claim 1 wherein a first finger sleeve permits slidable insertion of the user's index finger, and a second finger sleeve permits slidable insertion of the user's middle finger.

14. The device of claim 1 wherein said one or more finger sleeves each has a first forward end and a second back end, said first end is open to permit slidable insertion of one or more of the user's fingers, and said second end is closed.

15. The device of claim 1 wherein the device is packaged for sale, storage and user retention in an enclosed storage container having a first slot opening to access at least one device stored inside said container, and a second slot opening to a discard enclosure within said container, said device being dispensed out of the first slot opening and optionally discarded by insertion inside the discard enclosure.

16. The device of claim 1 wherein said device includes structures to assist the user to hold the device open in a use configuration.

17. The device of claim 1 wherein said discharge opening includes opposed, generally vertically-oriented tabs for urine stream control.

18. A water-resistant, collapsible, female urination aid and absorbent wiping device comprising:
 a) generally triangular-shaped first and second spaced side walls, said side walls having a generally inclined bottom edge, a generally vertical forward edge, and an upper margin;
 b) said side walls are joined along their bottom edges by a generally triangular-shaped center fan fold section;
 c) said side walls and fan fold section are made of flexible, self-supporting material having an external surface and an internal surface;
 d) said first and second side walls are joined along the forward edge to form a collapsible seam;
 e) said fan fold section comprising at least one pair of joined, converging panels forming at least one collapsible and expandable pleat for spacing said side walls apart to receive urine onto said fan fold's internal surface, said fan fold section converging toward a second apex end adjacent the seam;
 f) a discharge opening formed adjacent the intersection of said forward edge and said fan fold section apex for discharging urine from said device away from a user;
 g) at least a portion of said internal surface having water-resistant properties; and,
 h) at least a portion of said exterior surface having water-absorbent properties to provide a post-urination wiping surface.

* * * * *